United States Patent [19]

Clark, Jr.

[11] Patent Number: 5,536,753

[45] Date of Patent: *Jul. 16, 1996

[54] STABLE PERFLUOROCARBON AND OIL EMULSIONS

[75] Inventor: Leland C. Clark, Jr., Cincinnati, Ohio

[73] Assignee: Children's Hospital Research Foundation, a division of Children's Hospital Medical Center and HemaGen/PFC, Cincinnati, Ohio

[*] Notice: The term of this patene shall not extend beyond the expiration date of Pat. No. 5,514,720.

[21] Appl. No.: 611,332

[22] Filed: Nov. 9, 1990

Related U.S. Application Data

[63] Continuation of Ser. No. 464,647, Jan. 11, 1990, abandoned, which is a continuation of Ser. No. 346,340, Apr. 28, 1989, abandoned, which is a continuation of Ser. No. 235,837, Aug. 18, 1988, abandoned, which is a continuation of Ser. No. 822,291, Jan. 24, 1986, abandoned.

[51] Int. Cl.$^6$ .................................................. A61K 31/03
[52] U.S. Cl. ............................................................ 514/749
[58] Field of Search ................................. 514/756, 832, 514/749

[56] References Cited

U.S. PATENT DOCUMENTS

| | | | |
|---|---|---|---|
| 3,911,138 | 10/1975 | Clark, Jr. | 514/832 |
| 4,105,798 | 8/1978 | Moore et al. | 514/832 |
| 4,289,499 | 9/1981 | Clark et al. | 23/230 B |
| 4,395,393 | 7/1983 | Schmolka | 514/756 |
| 4,439,424 | 3/1984 | Ecanow et al. | 514/832 |
| 4,443,480 | 4/1984 | Clark, Jr. | 514/832 |
| 4,461,717 | 7/1984 | Moore | 514/832 |

OTHER PUBLICATIONS

"The Synthesis and Biological Screening of New and Improved Fluorocarbon Compounds for Use as Artificial Blood Substitutes", Final Report prepared under Contract # 14B6-2927 for the period Jun. 30, 1976–Dec. 31, 1978 by Robert E. Moore, as Prepared for the National Institutes of Health.

Yamanouchi, Kouichi et al, Chem. Pharm. Bull., 33(3) 1221–1231 (1985) "Quantitative Structure in Vivo Half-life Relationships of Perfluoro-chemicals for use as Oxygen Transporters".

*Primary Examiner*—Raymond Henley, III
*Attorney, Agent, or Firm*—Wood, Herron & Evans

[57] ABSTRACT

Perfluoroindane is used as a gas transport agent in animals without causing gas or vapor pulmonary embolism. Emulsions containing perfluoroindane as the oxygen carrying component are made and infused into an animal and the perfluoroindane escapes at a very rapid rate from the animal body. The perfluoroindane-containing liquids or emulsions are considered valuable for angioplasty and as a blood substitute.

7 Claims, No Drawings

STABLE PERFLUOROCARBON AND OIL EMULSIONS

This application is a continuation of application Ser. No. 07/464,647, filed Jan. 11, 1990, now abandoned.

BACKGROUND OF THE INVENTION

The oxygen carrying capacity and lack of toxicity of perfluorinated liquids has long been established. Emulsions of fluorocarbon liquids were also used as artificial bloods. U.S. Pat. No. 3,911,138 which issued to Leland C. Clark, Jr., sets forth the various advantages and needs for artificial blood and may be referred to as further background of this invention. In that Clark patent, artificial bloods containing perfluorocyclocarbons were disclosed as useful blood substitutes. Emulsions containing emulsified particles of the perfluorocyclocarbons were also infused intravenously into experimental animals and functioned as oxygen-carbon dioxide carrying agents intravascularly. The perfluorocyclocarbons disclosed in that Clark patent were referred to as RES-phobic, which indicated that the perfluorocyclocarbons exhibited a unique property of temporary sequestration by the liver or spleen and subsequent elimination by the animal body. It was later disclosed in U.S. Pat. No. 4,150,798 which issued to Leland C. Clark, Jr. et al, that certain other perfluoropolycyclic compounds were useful as synthetic blood in perfusion media. The perfluorinated polycyclic compounds disclosed in this patent are known generally as bicyclononanes and adamantanes. Further improvements have been reported in the patent art as disclosed in U.S. Pat. No. 4,443,480 which issued to Leland C. Clark, Jr. and is directed to oxygen transport agents containing a perfluorocyclocarbon and an organoamine oxide.

The brief reference to patents herein is intended only as background information leading up to this invention and is not intended to be exhaustive of the patent art. On the literature side of the prior art, reference may be made to such articles as "The Synthesis and Biological Screening of New and Improved Fluorocarbon Compounds for Use as Artificial Blood Substitutes", Final Report prepared under Contract No. 1HB6-2927 for the period Jun. 30, 1976–Dec. 31, 1978 by Robert E. Moore, Principal Investigator, as prepared for the National Institutes of Health. In this report, a number of fluorocarbons were reported as having been evaluated biologically for use in experimental animals. The biological evaluations were performed under the direction of Leland C. Clark, Jr., Ph.D. Among the approximately thirty fluorocarbons reported upon was bicyclo[4.3.0.] nonane, or otherwise known as perfluoroindane. However, perfluorindane was not considered to be viable choice, principally because it had a high vapor pressure of 32.8 mm at 37° C. This value was the highest among the perfluorinated hydrocarbons reported upon in the above NIH report. It was then believed that such a high vapor pressure would cause gas embolism, consistent with earlier reports in Clark U.S. Pat. No. 3,911,138 for other analogous carbon-containing perfluorocyclo derivatives such as perfluorotrimethylcyclohexane and perfluoroisopropylcyclohexane. In the event emulsions containing such perfluorocyclohexanes were used, then breathing the vapor of the fluorocarbons, or similar fluorocarbons, that were injected balances the gas pressures in the lungs so that gas embolism does not occur. Without this gas or vapor breathing, partial pressure of the fluorocarbons in the lungs is, unlike most other gases and vapors, extremely low apparently due primarily to the poor solubility of the fluorocarbon in the blood; and its slow diffusion from the blood through the lung membrane. Hence, the total gas pressure in the blood exceeds total alveolar pressure, and gas embolism results which could lead to death in a short time. Thus, perfluorocyclocarbons that have lower vapor pressures than perfluorocyclohexanes were considered critically necessary in order to avoid special precautions or detrimental gas embolism.

About ten years has elapsed since the above mentioned NIH report upon the use of perfluorocarbons as oxygen transporting agents in animals. More recently, it has been reported by Kouichi Yamanouchi et al in *Chem. Parm. Bull.*, 33(3)1221–1231(1985) entitled "Quantitative Structure in Vivo Half-Life Relationships of Perfluorochemicals for Use as Oxygen Transporters" that a series of perfluorochemicals were investigated in terms of their quantitative structure-activity relationships. Among other findings reported in this paper, it was concluded that the vapor pressure of perfluorocarbons apparently plays an important role in the excretion system and it must be controlled within an acceptable limit so as not to cause lung damage.

SUMMARY OF THE INVENTION

This invention is predicated in part upon the use of perfluoroindane as a gas transport agent in animals without causing gas or vapor pulmonary embolism. Evidence has led to the conclusion that perfluoroindane does not cause gas or vapor pulmonary embolism and such a result is considered to be an unexpected and important finding. Perfluoroindane has been found to have many advantages as a potential candidate for artificial blood. It leaves the body about five times faster than perfluorodecalin and makes an emulsion having about the same qualities as perfluorodecalin which up to this time has achieved the most clinical usage in humans. When given intravenously to mice as an emulsion, perfluoroindane does not show signs of toxicity and there is no evidence of gas/vapor embolism. The activities of perfluoroindane are considered to be unexpected, especially, when compared to its two close relatives, namely, perfluorotrimethylcyclohexane and perfluoroisopropylcyclohexane.

In one form of the invention, perfluoroindane is emulsified in water with a suitable surfactant. In another form, perfluoroindane is emulsified in a previously prepared intravenous emulsion. Emulsions containing from about 10 or 20 to about 50% or more of the perfluoroindane by volume in water may be prepared. Emulsifying agents are included on the order of about 1 to 10%, exemplified by egg phosphatide, phospholipid or polyoxyethylene-polyoxypropylene copolymer and mixtures thereof having a molecular weight of about 8200 (Pluronic F-68). Other types of surface active agents may be used, including, albumin, glycerol, dextrans, gelatin, or other naturally occurring surfactants. The nonionic surfactants, which do not cause hemolysis, are preferred. In addition to the perfluoroindane and surface active agent in the emulsion, it is preferred, but not essential, that the emulsion include an ionic component. Because most of the surfactants have sizeable osmotic activity, some consideration has to be given to modifying the ionic composition so as not to have a hypertonic solution. Generally speaking, in the preparation of emulsions, there is added approximately 0.6 to 0.9% by weight sodium chloride since this is a concentration which can be infused rather rapidly without causing hemolysis. Ringer solution as is or diluted to half-strength with water is suitably used.

In another form of the invention, oxygen transport is facilitated in the coronary artery by the introduction of perfluoroindane or liquid compositions containing perfluoroindane. In a further form of the invention, an isolated organ of an animal may be perfused with a perfluoroindane or liquid composition containing same. Furthermore, the perfluoroindane compositions of this invention may be employed utilizing NMR techniques according to procedures reported in my pending U.S. patent application Ser. No. 472,229, filed Mar. 4, 1983, now U.S. Pat. No. 4,586,511, issued May 6, 1986.

Perfluoroindane, after intravenous infusion as an artificial blood, also has the unique property of exiting from or being excreted by the animal body by way of the tissue, for example, the lungs and the skin. It has been found that the cis form of perfluoroindane leaves faster than the trans form. Separation of the cis from the trans forms may be obtained if it is desired to utilize this property of the perfluoroindane molecule.

This invention and its principles will be further understood with reference to the following operating examples.

EXAMPLE 1

An emulsion of perfluoro-cis-indane was prepared by mixing 10% by volume of the perfluoroindane in an intravenous fat emulsion, i.e., LIPOSYN II, manufactured by Abbott Laboratories. The LIPOSYN II is supplied in 10 and 20% concentrations. In this example, 10% concentration of LIPOSYN II is employed and contains 5% safflower oil, 5% soybean oil, up to 1.2% egg phosphatides added as an emulsifier and 2.5% glycerin in water for injection. Sodium hydroxide has been added to adjust the pH to approximately 8.0 LIPOSYN II 10% has an osmolarity of 320 mOsm/liter (approximate). The total caloric value of LIPOSYN II 10% including fat, phospholipid and glycerol is 1.1 kcal/ml. Of this total, approximately 0.6 kcal/ml is supplied by linoleic acid.

The perfluoroindane emulsion in this example was then injected into mice at a dose of 20 cc/kilogram of body weight intravenously. Upon intravenous injection, there were no signs of toxicity and no evidence of gas or vapor embolism. It was also determined that the perfluoroindane left the animal body about five times faster than perfluorodecalin.

More specifically, the average transpiration rate in microliters per day for perfluoroindane decreased from about 30 microliters/day upon infusion to a level of about 5 microliters/day at day 2, followed by rapid diminishment to less than 1 microliter/day after day 3.

By comparison, perfluoro-1,3,5-trimethylcyclohexane was emulsified in a similar fashion at a level of about 10% by volume within 10% LIPOSYN II and injected into mice at a dose level of about 20 cc/kilogram intravenously. The average transpiration rate in microliters/day was observed at a level of about 10 immediately after infusion to a level of about 5 microliters/day after day 1, and about 2½ microliters/day after day 4. By comparison, therefore, the transpiration rate of perfluoroindane is considerably faster than the rate for perfluorotrimethylcyclohexane which is considered an analog or sister compound.

In a similar fashion, perfluoroisopropyl-cyclohexane was emulsified at a level of about 10% by volume with 10% LIPOSYN II and mice were injected at a dose of about 20 cc/kilogram intravenously. As expected, the transpiration rate of the perfluoroisopropylcyclohexane was essentially the same as that for perfluorotrimethylcyclohexane. However, by comparison perfluoroindane has an unexpectedly faster rate of transpiration or elimination from the body of the mouse.

This example thus demonstrates that perfluoroindane may be injected into the animal body without causing gas or vapor embolism. Moreover, emulsions of perfluoroindane may be made and infused intravenously to function in a gas transport manner without toxic effects. Furthermore, upon comparison with analogous compounds, quite unexpectedly, the transpiration rate is significantly faster.

EXAMPLE 2

The procedures of Example 1 for perfluorocis-indane were repeated except that mice were injected with a dose of 40 cc/kilogram intravenously of the 10% by volume emulsion with 10% LIPOSYN II.

Similar transpiration rates were observed with the larger dose of perfluoroindane except that larger amounts of perfluoroindane were being transpired post injection, namely, about 30 microliter/day at about day 1, about 17 microliter/day at day 2, about 10 microliters/day at day 3, about 4 microliters/day at day 4 and nearly 0 microliters/day at day 7. Otherwise, the experiments with mice injected at a level of 40 cc/kilogram intravenously produced essentially the same results as those at the lower dose of 20 cc/kilogram according to Example 1.

Having described this invention and exemplified it, it will be understood to a person of ordinary skill in the art that variations may be made without departing from its true spirit and scope.

What is claimed is:

1. A physiologically acceptable aqueous emulsion of a perfluorocarbon comprising a perfluorocarbon, an oil that is not substantially surface active and not significantly water soluble, a surfactant and water, wherein the emulsified perfluorocarbon is present in the emulsion in an amount of about 20 to about 50% or more by volume.

2. The emulsion of claim 1 containing about 1 to about 10% surfactant and about 10 to about 20% oil.

3. The emulsion of claim 1 wherein said oil comprises a triglyceride of fatty acids.

4. The emulsion of claim 3 wherein said oil is selected from the group consisting of safflower oil, soybean oil and mixtures thereof.

5. A physiologically acceptable aqueous emulsion of a perfluorocarbon comprising (a) a perfluorocarbon emulsified in an amount between about 20 to about 50% or more by volume, (b) an oil comprising a triglyceride of fatty acids in an amount from about 10 to about 20%, (c) a surfactant in an amount from about 1 to about 10%, and (d) water.

6. The emulsion of claim 5 wherein the oil is selected from the group consisting of safflower oil, soy bean oil, and mixtures thereof.

7. The emulsion of claim 5 wherein said perfluorocarbon is selected from the group consisting of perfluoroindane, perfluorotrimethylcyclohexane, perfluoroisopropylcyclohexane and perfluorodecalin.

* * * * *